(12) United States Patent
Price

(10) Patent No.: US 6,734,795 B2
(45) Date of Patent: *May 11, 2004

(54) LOCATION OF LOST DENTURES USING RF TRANSPONDERS

(76) Inventor: William Raymond Price, 1452 Ridgemere La., Winston-Salem, NC (US) 27106

( * ) Notice: Subject to any disclaimer, the term of this patent is extended or adjusted under 35 U.S.C. 154(b) by 97 days.

This patent is subject to a terminal disclaimer.

(21) Appl. No.: 09/925,908

(22) Filed: Aug. 9, 2001

(65) Prior Publication Data

US 2002/0017998 A1 Feb. 14, 2002

Related U.S. Application Data

(60) Provisional application No. 60/224,268, filed on Aug. 10, 2000.

(51) Int. Cl.[7] ............................................. G08B 13/14
(52) U.S. Cl. ..................... 340/572.1; 340/573.8; 340/539.32; 340/825.49; 324/239; 433/229
(58) Field of Search .................. 340/572.1, 572.8, 340/5.8, 5.2, 573.1, 573.3, 573.4, 568.1, 539, 825.49, 539.1, 539.13, 539.32; 324/239; 433/229, 167, 171, 215, 199.1, 200.1, 195; 343/873; 542/46

(56) References Cited

U.S. PATENT DOCUMENTS

| | | | |
|---|---|---|---|
| 3,836,842 A | * | 9/1974 | Zimmermman et al. .... 324/239 |
| 5,037,301 A | | 8/1991 | Michnick et al. ........... 433/229 |
| 5,214,410 A | * | 5/1993 | Verster ........................ 340/505 |
| 5,392,028 A | * | 2/1995 | Pichl ........................ 340/572.5 |
| 5,760,692 A | | 6/1998 | Block ........................ 340/573.1 |
| 5,798,693 A | * | 8/1998 | Engellenner ................ 340/505 |
| 6,025,780 A | * | 2/2000 | Bowers et al. ........... 340/572.3 |
| 6,059,571 A | | 5/2000 | Kishigami .................. 433/167 |
| 6,239,705 B1 | | 5/2001 | Glen ........................ 340/573.1 |
| 6,366,206 B1 | * | 4/2002 | Ishikawa et al. ......... 340/573.1 |
| 6,400,338 B1 | * | 6/2002 | Mejia et al. ................ 343/873 |
| 6,447,294 B1 | * | 9/2002 | Price ........................ 433/167 |

* cited by examiner

Primary Examiner—Benjamin C. Lee
(74) Attorney, Agent, or Firm—Robert W. Pitts

(57) ABSTRACT

A locator or signaling device and a detector system for locating lost dentures includes a button or insert that can be mounted on the surface of an existing denture. An insert can also be implanted in a new denture. The internal signaling component is surrounded by a resin layer that can be used to bond the locator button to the existing denture and will also isolate the internal signaling component form the denture wearer's oral cavity. The internal signaling component is responsive to an electromagnetic field and emits a detectable signal when the denture is located with a specified interrogation zone or search area. Signaling components having magnetic characteristics that are altered by an incident variable electromagnetic field can be employed. The preferred location for the locator, locator strip, marker or button is on the interior lingual surface of the flange of a mandibular or lower denture. The denture can also include an RF passive transponder embedded therein which can be detected at short range by a portable detector. The RF passive transponder includes a logic component having a unique code that is transmitted when the denture is subjected to an electromagnetic field emitted by the portable detector.

12 Claims, 13 Drawing Sheets

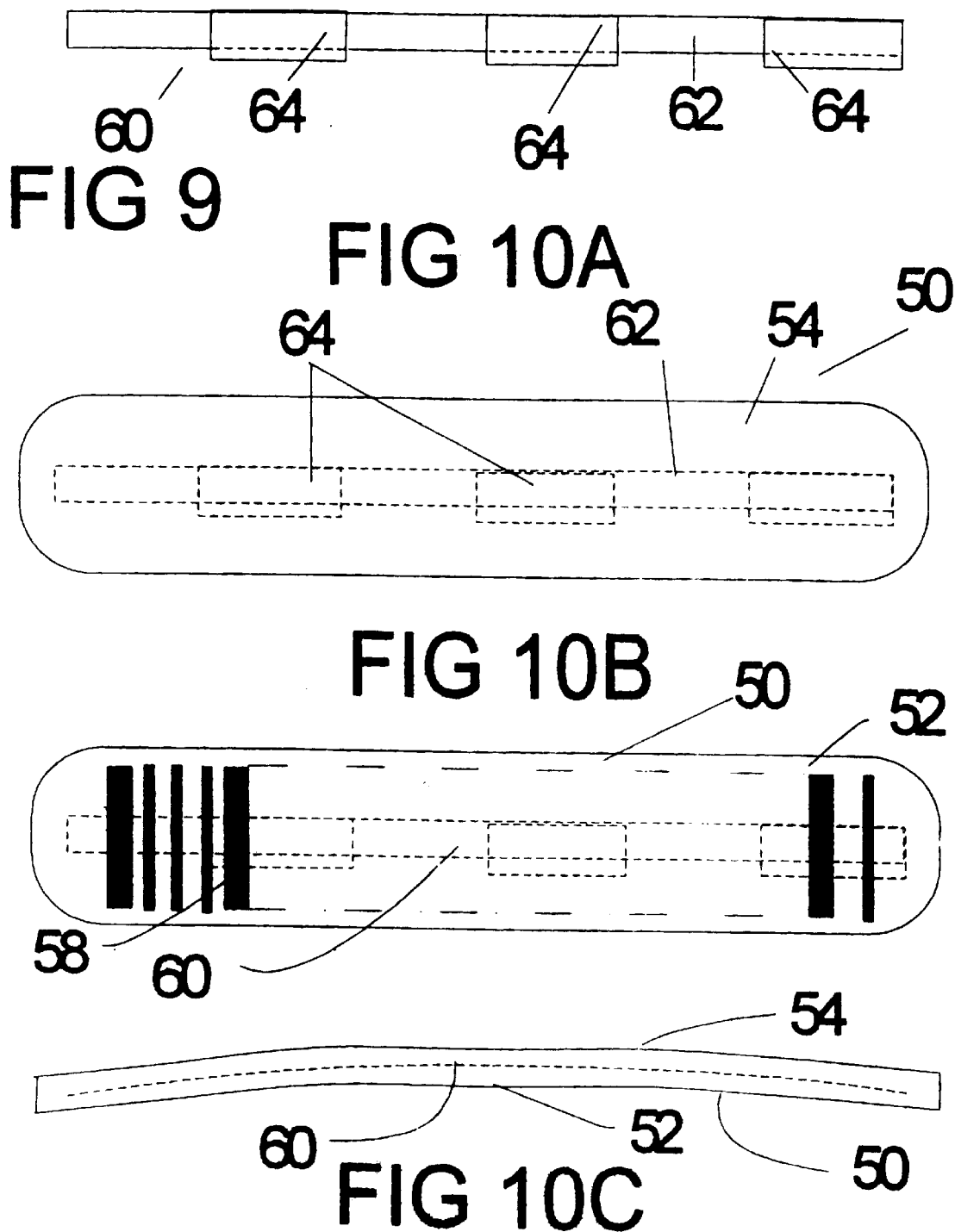

LOCATION OF LOST DENTURES USING RF TRANSPONDERS

CROSS REFERENCE TO PRIOR CO-PENDING APPLICATION

This application claims the benefit of prior co-pending Provisional Patent Application Serial No. 60/224,268 filed Aug. 10, 2000.

BACKGROUND OF THE INVENTION

1. Field of the Invention

This invention is related to dentures and to an apparatus and method for locating lost dentures. This invention is also related to a signaling device that can be mounted in existing dentures or incorporated in new dentures and to a detector for locating the signaling device, attached to the lost denture within a certain area or an interrogation zone. The detector area or interrogation zone could be located at a building exit leading to a trash disposal collection area.

2. Description of the Prior Art

Medical institutions and long term care facilities in which patients and residents may suffer from diminished mental capacity or simple forgetfulness frequently have difficulty locating personal articles that have been misplaced or lost. One problem that is often encountered is that the patients or residents tend to lose or misplace their dentures. Patients or residents in such facilities often inadvertently throw their dentures in trash receptacles, leave them in pockets of clothing that is taken to a laundry facility or leave then on serving trays after meals. In rest homes and nursing care facilities, the resident may also place the dentures under sheets, in closets or in drawers where they can be difficult to locate. In some cases, the dentures are subsequently located by the institution's personnel, who cannot identify the owner. In other situations the lost dentures are inadvertently disposed of in the trash or simply cannot be found within a reasonable time.

Although this problem occurs even when the institutions personnel are vigilant, it is especially upsetting to the residents and to their relatives. Lost dentures can be costly to replace, and relatives can be especially upset that the institution cannot keep track of their older relative's dentures. In many cases, the institution must replace the dentures and is not reimbursed.

Medical institutions do encounter problems with lost articles in other contexts. For example, U.S. Pat. No. 5,923,001 discloses a surgical sponge detection system for use in an operating room in which detectable RF tags are attached to the sponges. U.S. Pat. No. 5,664,582 discloses a marker that can be used on a surgical instrument. However, these devices are used only within a controlled environment, and the problem of lost dentures arises because it is not possible to control the environment in which the loss may occur.

U.S. Pat. No. 4,160,971 discloses a passive transponder without a local power supply that is remotely powered by received transmissions. This device is primarily intended to measure pressure on dental plates. However, this device is intended to provide telemetry instead of a locator signal and it does not appear to be adapted for incorporation into denture that would be used for an extended period of time by an ordinary denture wearer. It also does not to be adapted for use with an existing denture.

Implants for use in a prosthesis are shown in U.S. Pat. No. 5,300,609 and in U.S. Pat. No. 5,855,909. However, these devices are also intended for data transmission instead of as a locator, and as such would not have the range to locate lost dentures.

SUMMARY OF THE INVENTION

A denture in accordance with the instant invention has base and teeth, including molar teeth, with a cylindrical glass encapsulated transponder embedded in the lingual flange of the denture adjacent molars mounted on the denture base. The transponder is covered by a denture material conforming to the contour of surrounding areas of the denture base, and the transponder emits a signal that can be remotely detected so that the denture can be found when lost.

The passive transponder can be mounted in a denture by forming a trench in a lingual area of a denture base adjacent molars on the dentures. The trench extends to a rear edge of the denture base. The transponder is then placed in the trench, and the trend is then filled to secure the transponder in the denture base.

This denture with a passive RF transponder can then be used in a system for locating a lost denture. The RF passive transponder contains an integrated circuit device connected to a coil. A reader having a transceiver for emitting an electromagnetic field is also used in the system. The electromagnetic field results in the generation of a voltage in the coil so that a code stored on the integrated circuit device is then transmitted through the coil to the transceiver for detecting the presence of a lost denture containing an RF passive transponder within a localized area.

BRIEF DESCRIPTION OF THE DRAWINGS

FIG. 9 is a view of a passive signaling device including a magnetic strip whose presence can be detected by its response to variations in an external electromagnetic field, and also includes a number of other magnetic elements that can be used to deactivate the primary magnetic strip.

FIGS. 10A, 10B, and 10C are views showing the exterior of a representative insert or button that would be placed on a preexisting denture. FIG. 10A shows a roughened face of the insert that will be bonded to the denture. FIG. 10B shows a smooth surface on the opposite side that would be exposed and will conform to the shape of the denture. FIG. 10C is an edge view of the denture showing a shape that would correspond to the shape of a portion of the denture.

DETAILED DESCRIPTION OF THE PREFERRED EMBODIMENT

Figure 1:
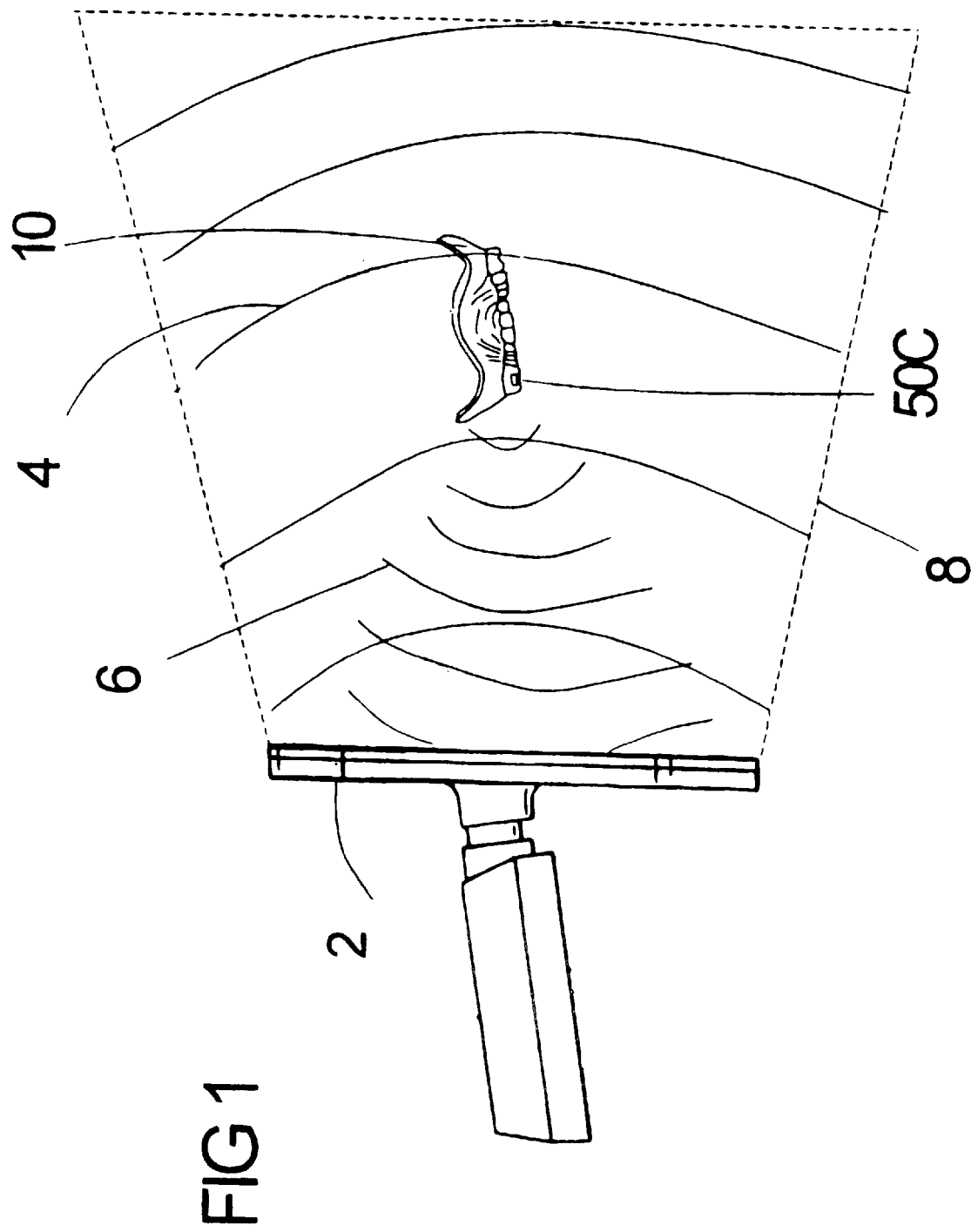
FIG. 1 is a schematic view of a portable detection unit that would be used to locate a lost denture which includes a device emitting a signal in response to a field transmitted by the detection unit.

FIG. 1 is a schematic view showing basic components of a system for locating a denture that has been lost by a patient confined to a medical institution. This system includes a transmitter-detector unit or transceiver 2 which is capable of identifying a signaling device, here represented by device 50C, that is mounted on or included in the denture 10. In this representative embodiment, the transmitter-detector 2 emits an electromagnetic field or excitation field, represented by wave fronts 4, which impinge upon the signaling device 50C. The signaling device contains an internal component that is activated by the external electromagnetic field 4 and emits a signal, represented by return wave front 6 which is in turn detected by the detection circuit in the transmitter-detector 2. The strength of the excitation field 4 and the sensitivity of the signaling device 50C are chosen so that the lost denture 10 can be detected if the denture 10 is within a specified interrogation zone, represented by the boundary 8. Preferably this interrogation field has a radius of approximately three feet from the transmitter-detector unit 2 so that a suitable large area can be searched while still keeping the search area small enough to permit an effective search once the lost denture 10 has been detected within the search area. Although a search area having a radius of at least three feet is desirable, this invention is also applicable to systems having either larger or smaller search areas or interrogation zones. Portable transmitter detector units with an even more limited range can be employed because the searcher is mobile and can search a suspected area by placing the detector unit in close proximity to areas where the denture might be located. In a system that also employs stationary detector units, stationary detectors units can be used to monitor areas through which lost denture might be expected to pass, such as an exit to a garbage collection area. The portable units, even with very limited range, can be used to search specific areas, such as a room or closet, where there is a strong possibility that the lost denture might be found.

The preferred embodiment employs a passive signaling device 50 that emits a detectable signal only when subjected to a transmitted excitation field 4. Preferably this passive signaling device 50 does not include its own energy source, such as a battery, because a battery will increase the size of the passive signaling device 50 and a battery will have a finite life. In many cases a relative long time elapses between attachment of the signaling device 50 to the denture or incorporation of the signaling device 50 in the denture and the first time that the denture is lost. There may however be certain limited applications in which an active signaling device could be employed.

The transmitter-detector 2 depicted in FIG. 1 is intended to be a portable device that can be used to search several areas, such as different rooms in a medical institution. It should, however, be understood that stationary transmitter-detector units 2 would also be useful. For instance in a long term care facility a stationary unit could be located at the entrances and exits to dining facility, in laundry areas, in a trash disposal facility and near dishwashing facilities. When used in such applications the transmitter-detector units 2 should be activated only at certain times. For instance, when used in a dining area, the transmitter-detector 2 would be activated only when dishes and trays, where lost dentures 10 could likely be inadvertently placed, are removed from the dining area. This capability would limit false alarms as patients wearing dentures enter and exit the dining area. The transmitter-detector 2 is also not limited to devices in which both the transmitter and the detector are located within the same physical structure. Separate transmitter and detection units could also be employed. For example a transmitter could be located on one side of a doorway and the detector could be place on the opposite side. For portable units, one of two separate units could be located at one point while the other unit would be moved in a circle around the unit that is not moved. FIG. 1 shows only a single denture within the interrogation zone 8. However in many cases, both the upper and lower denture would be lost and by including signaling devices or locators or both dentures, the overall size of the locator could be greater than would be practical for a single locator of a size suitable for one denture, and therefore for some detection technologies, the size of the interrogation zone or search area could be larger.

Although signaling devices 50 could be embedded in a dentures when they are initially fabricated, the typical use of this system will be to detect previously fabricated dentures. This is especially true because the most frequent application of this device will be in a medical care facility, and most denture wearers will be fitted with artificial dentures long prior to entry into such a facility. FIGS. 2–7 show areas in which signaling devices 50 can be mounted on or encapsulated in either a maxillary or upper dentures 10 or mandibular or lower dentures 20.

Figure 2:
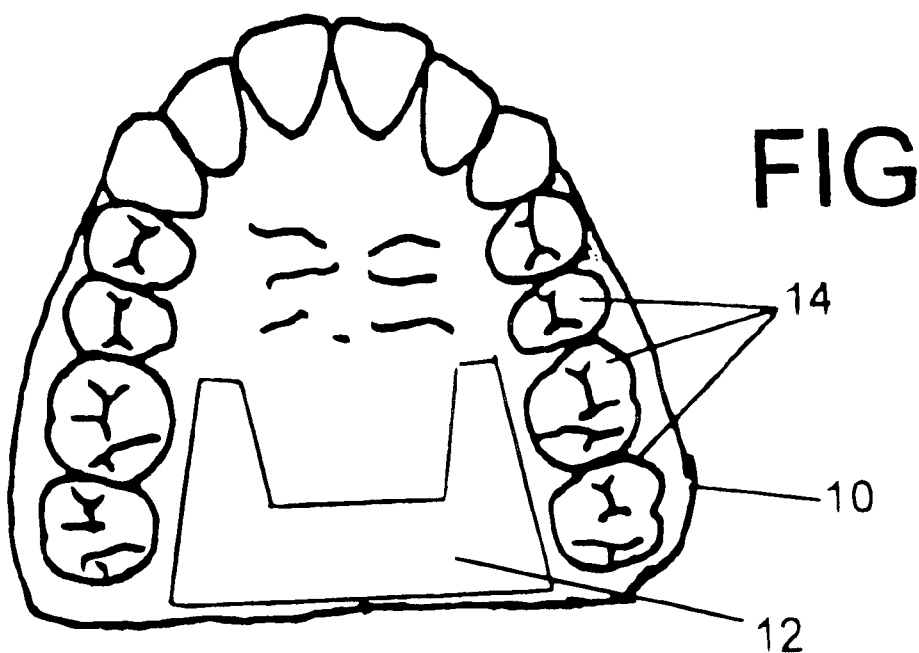
FIG. 2 is a view of the interior of a maxillary or upper denture showing an area in which a device can be mounted without adverse effects on the user's oral cavity or tongue.

FIG. 2 shows the lower or exposed area of a maxillary denture 10. The area 12 outlined at the rear of the denture 10 is located in the palatal vault area of the upper denture 10. If a signaling device 50 is mounted in this area, it will not irritate the oral cavity or the tongue of the denture wearer, provided that the signaling device 50 is not too thick and does not protrude substantially from the adjacent surface of the palatal vault area. A locator or signaling device 50 positioned within this area could have different shapes.

Figure 3:
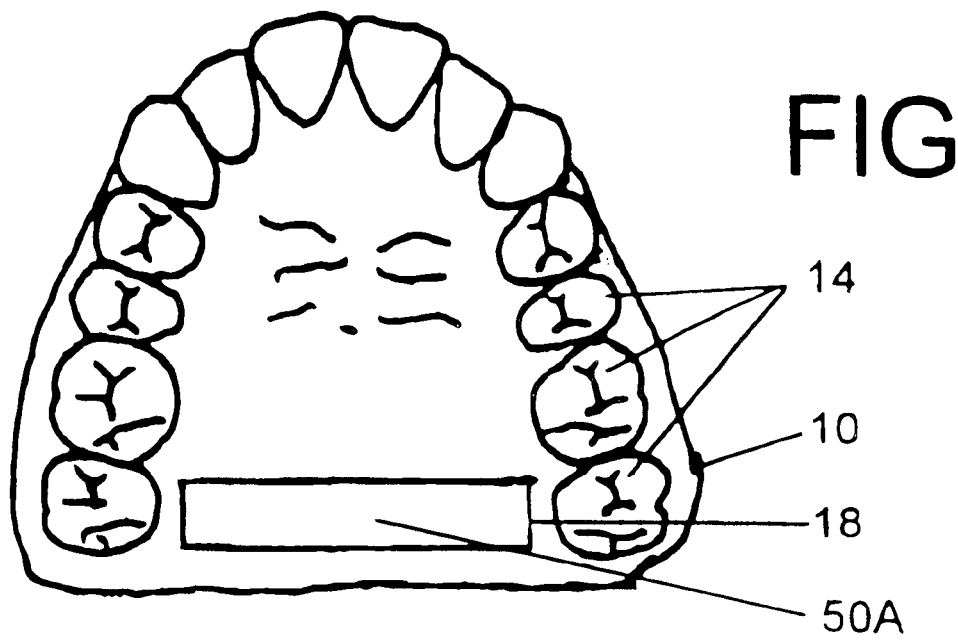
FIG. 3 is a view of a representative passive device mounted in the palatal vault of a maxillary denture.
Figure 4A:
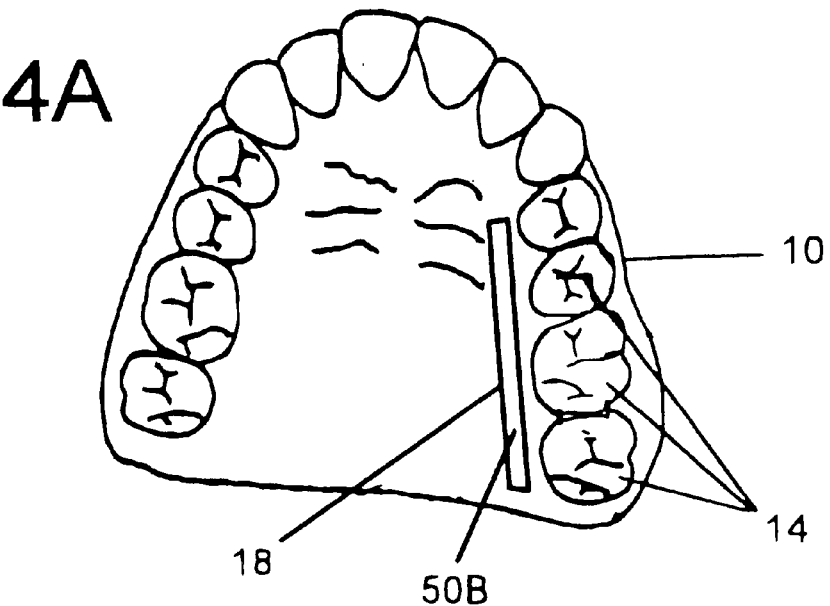
FIGS. 4A and 4B are views of another location in which another representative passive device can be located on the interior of the lingual flange area of a maxillary or upper denture.
Figure 4B:
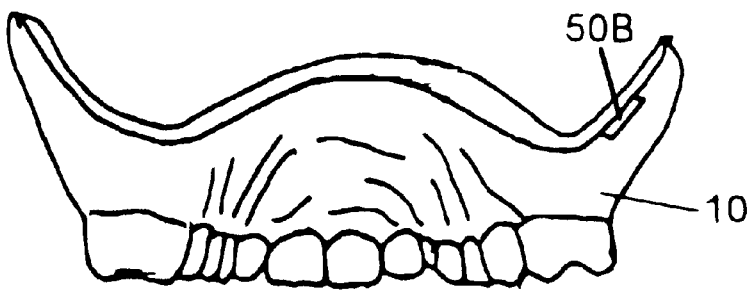

A signaling device 50A in the form of a button or insert having dimension of 3 mm×8 mm×40 mm could be located adjacent to and along the rear edge of the palatal vault area of the maxillary denture 10 in the manner shown in FIG. 3. This area would extend generally between the rearmost molars 14 on this upper denture 10. The thickness of this locator 50A would be less than the local thickness of the denture where the locator would be positioned. FIGS. 4A and 4B shows a signaling device 50B located along the interior lingual flange on one side of the maxillary denture 14. A signaling device 50B could also be located on the opposite side of the palatal vault area. A signaling device 50B having the dimensions of 7 mm×20 mm×2 mm could be located in this area. A device 50B located in this area could would be located along a flat surface of the posterior palate, but signaling device 50B cannot be allowed to intrude in the normal space for the dorsal side of the tongue and signaling device 50B cannot penetrate the palatal surface since this would cause irritation of the dense palatal tissue of the denture wearer. Both buttons 50A and 50B are shaped so that the exposed surface generally conforms to the local surface 18 of the denture 10, so that the button 50A can be firmly affixed to the denture without protruding too far into the denture wearer's oral cavity.

Figure 5A:
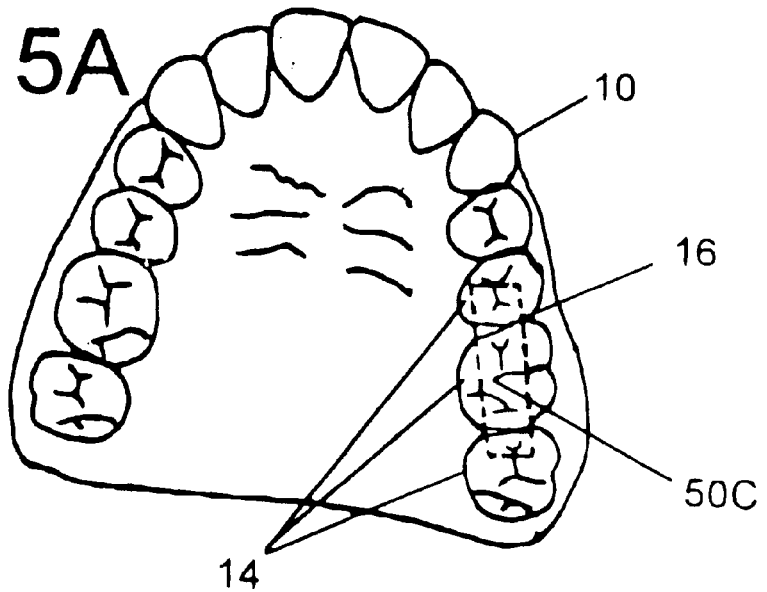
FIGS. 5A and 5B are views of a cavity that can be located below the molar teeth area of a maxillary denture, and which can provide space for a representative passive signaling device.
Figure 5B:
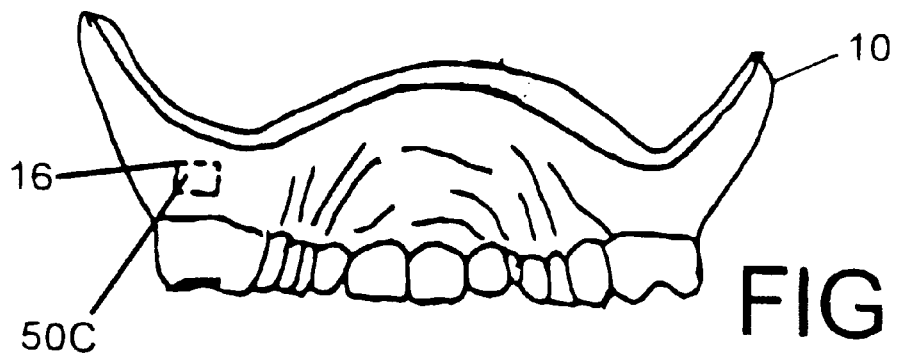

An alternative location for a signaling device 50 in the form of a button or insert is shown in FIGS. 5A and 5B where a signaling device 50C is located between the molar teeth and the gum surface of the maxillary denture. This location would be especially suitable for a denture in which the signaling device is positioned in the denture when the denture is initially manufactured in a dental lab.

Figure 6A:
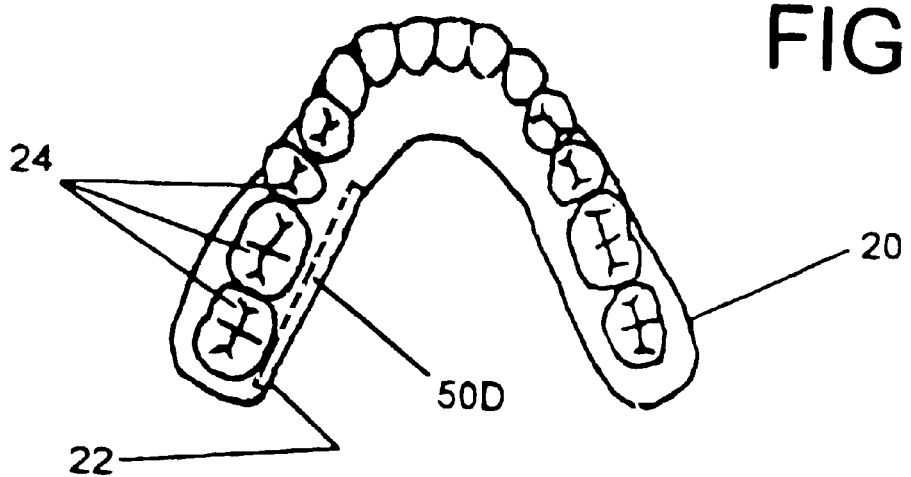
FIGS. 6A and 6B are views of a representative device located on the lingual flange area of a mandibular or lower denture.
Figure 6B:
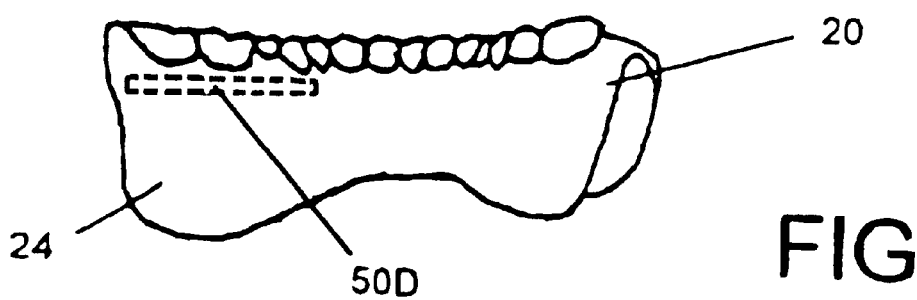
Figure 7:
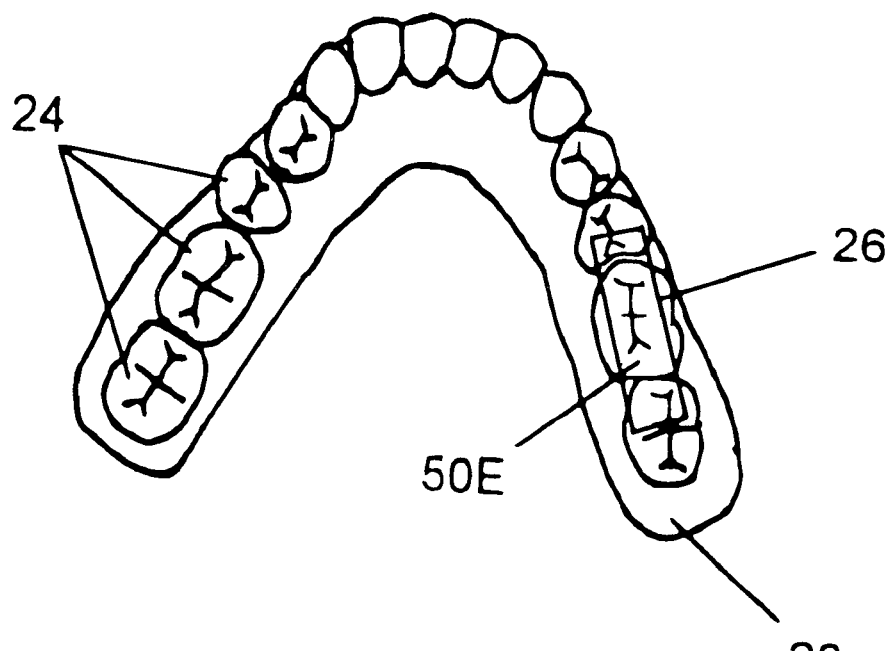
FIG. 7 is a view of a cavity in the molar teeth area of a mandibular denture in which a representative device responsive to an interrogation field can be located.
Figure 8:
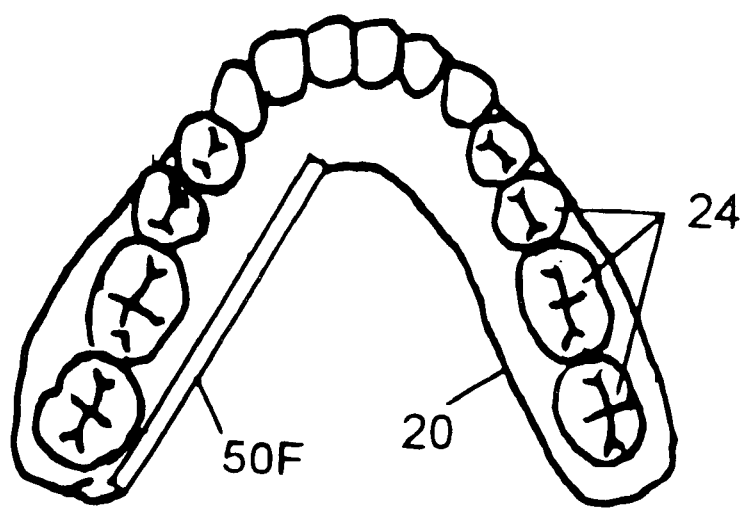
FIG. 8 is a view of another signaling device that can be mounted along one side of the lower denture.

Signaling devices can also be mounted on a mandibular or lower denture 20 as shown in FIGS. 6–8. The device 50D, shown in FIGS. 6A and 6B, is positioned on the lingual surface of the flange of the mandibular denture 20 in the base portion of the denture below the teeth.

FIG. 7 is another view of a button 50E located on the lower denture 20. This button 50E is located within a molar cavity 26 formed between lower molars 24 on one side of the denture 20 and the gum surface of the denture. As with the configuration shown in FIGS. 5A and 5B, material is removed from the denture behind the molars 24 to form the cavity 26. The signaling device 50E is then placed in the cavity 26 and a previously fabricated mold is used to restore the exterior surface of the molars 26.

FIG. 8 shows a third zone in which a signaling button 50F can be mounted on the lingual surface of the flange of the mandibular denture 20. It can be seen that the signaling button 50F is longer than the signaling button 50D shown in FIGS. 6A and 6B. FIG. 8 shows that some material can be removed from the lingual flange of the mandibular denture adjacent the front of the denture so that the button 50F will not protrude form the inner surface of the front denture at this location causing discomfort to the denture wearer.

FIG. 9 shows a passive magnetic strip 60 that is used in the preferred embodiment of this invention. These magnetic strips are commercially available from Sentry Technology Corporation and its subsidiary Knogo North America, Inc. and are referred to as Micro Magnetic strips. Micro Magnetic is believed to be a trademark of Sentry Technology Corporation. The magnetic strip 60 comprises two layers. The first layer 62 is a continuous thin strip formed from a soft magnetic material that has a relatively low coercivity so that the magnetic state of this strip 60 can be changed by the alternating magnetic field imposed by the varying electromagnetic field emitted by the transmitters in the transmitter-detector units. The second overlapping layer comprises a series of segments 64 that are formed from a second material that can occupy two different magnetic states. In one state, the low coercivity magnetic strip 62 is unaffected by the segments 64. When the segments 64 are in a second magnetic state, the magnetic field exerted by the segments 64 effectively prevents any changes in the magnetic state of the strip 62. Since the magnetic state of the strip 62 remains constant, no detectable signals are emitted by the strip 62 in response to a varying magnetic field to which the magnetic strip 60 is subjected. In one version of magnetic strips of this general type, the segments 64 can be magnetized so that the magnetic field exerted by the segments 64 is larger than the peak magnetic field exerted by the incident electromagnetic field on the strip 60. Thus the incident magnetic field is not strong enough to change the state of the soft magnetic material in strip 62. In alternative magnetic devices of this type, the magnetic field exerted by the second segments or strips on the variable magnetic strip, will bias the primary magnetic strip so that a distinctive response will be generated.

The segments 64 can be activated and deactivated by a separate apparatus that can be used to change the magnetic state of the segments 64 between an active and an inactive state. Typically the segments would be placed in a state corresponding to a device inactive state when the denture wearer would not be residing in a medical care facility to prevent inadvertent activation of transmitter-detector units that might be used for other purposes. The magnetic device 60 would be activated when the denture wearer is in a health care institution equipped with transmitter detector units to prevent inadvertent loss by the denture wearer. A system of this type would therefore permit installation of a signaling device 50 in a denture before the denture wearer moves to a health care facility. Of course this description applies to only one representative embodiment of magnetic strip signaling units that can be employed with this invention. For instance harmonic magnetic strips can be employed in addition to other configurations in which the magnetic field in altered when in the presence of a varying electromagnetic field.

There are a number of different materials that can be employed to fabricate the magnetic strip 62, or their equivalents, and the secondary segments 64, or their equivalents. Permalloy is one material that has been used for the primary magnetic strip, such as strip 62. Other similar strips use a material marketed by Allied Signal or Honeywell under the trademark Metglas. U.S. Pat. No. 5,029,291 discloses a cobalt alloy that can exhibit an asymmetric hysteresis characteristic and the response can be detected when subjected to a variable incident magnetic field. One material that can be used to form the segments 64 is iron oxide. Other material for fabricating magnetic detector strips of this type are also known to those of ordinary skill in the art.

FIGS. 10A through 10B show a dental locator strip 50 that employs the magnetic strip 60. The dental locator strip 50 includes a resin layer that encapsulates the magnetic locator strip 60 to protect both the denture wearer form the magnetic locator strip 60 and the strip form the acids or other contaminates that may be present in the denture wearer's oral cavity of from fluids that may be used to clean the denture. The resin used in the dental locator 50 can comprise a resin of the type typically used in dentures. The preferred embodiment of this invention employs methyl methacrylate as the resin surrounding the magnetic locator strip 60. The methyl methacrylate also serves to bond the dental locator 50 to the denture. An alternate material is (2-2-bis(4-(2-hydroxy-3-methacryloyloxy propoxy)phenyl)propane, commonly referred to as bis-GMA. Neither of these resins is ferromagnetic and the electromagnetic field can penetrate either resin so that the magnetic strip 60 will still be subjected to the incident variable electromagnetic field.

The interior side 54 of the dental locator strip 50, shown in FIG. 10A would either have a generally rough texture, or would be roughened prior to attachment to the denture so that the resin can be bonded to the denture. FIG. 10B shows the exterior smooth surface 52 of the dental locator 50 that will be exposed when the dental locator is bonded to the denture. This surface 62 will have a contour that will confirm to the local contour of the denture to which the dental locator 50 will be bonded. FIG. 10C shows that the exterior surface 52 will have a generally concave contour, although the precise shape of each dental locator 50 will conform to the local contour of the individual denture. The manner in which this shape is formed will be subsequently discussed in greater detail.

The exterior surface 52 of dental locator 50 also includes a visible indicia that will enable a lost denture to be identified when found. A representative bar code 58 is visible on surface 52. This bar code 58 will serve as a unique identifier for both the denture and the denture wearer so that a lost denture can be returned to its owner. In the preferred embodiment of the system of which each dental locator 50 is a part, a central database, including all dentures and denture owners, will be maintained. Of course individual databases could also be maintained at each health care institution.

Irrespective of the type of signaling component used in the signaling device 50, the device can be mounted on an exposed surface of an existing denture in the same manner. First the dental surface to which the signaling button 50 is to be attached is to be cleaned and sterilized. A groove or trench is then cut into the denture. This groove or trench is large enough to at least partially insert the dental locator 50 so that the exposed surface 52 will be substantially flush with the local contour of the denture when bonded to the denture. The surface of the locator zone or trench must then be primed with a liquid monomer of the acrylic that is used to encapsulate the dental locator strip. In most cases the material encapsulating the internal component will be methyl methacrylate, which is available as a liquid monomer and as a polymer powder. A liquid paste of monomer and polymer of the acrylic resin of the denture base and the capsule will be applied to the prepared denture and the previously roughened surface 54 of the dental locator strip 50. The dental locator will then be placed in the prepared zone and cured and finished in a smooth and polished surface in accordance with standard denture finishing procedures. Dentures and dental locators fabricated from methyl methacrylate can be cured in hot water and a chemical bond will be formed between the denture and the button. The button 50 will then be permanently bonded to an external surface of the denture in a location where the denture will not excessively protrude from the surrounding contour of the denture and will not cause discomfort to the denture wearer.

The visible mark, such as the bar code 58, shown in FIG. 10A can be used to identify the owner of each denture after it is found. Such a unique mark can be stored on a computer stored and accessible database which could include information in addition to the identify of the owner. Such an approach would permit entry of information to the database in a manner that the personnel at a medical institution would find familiar and would not require an special procedure for encoding an integrated circuit component or other codeable component. If such information is stored on a computer accessible database, that information can be made available to other institutions. For example if the database is accessible via the INTERNET or via a similar network, other institutions can easily access the information. For example if a nursing home patient is transferred to a hospital, where the denture is lost, the hospital can access data entered at the nursing home to identify the owner of a lost denture after it is found. Furthermore the database can include information that would permit a dentist to fabricate a new denture if the original is damaged beyond repair.

Figure 12A:
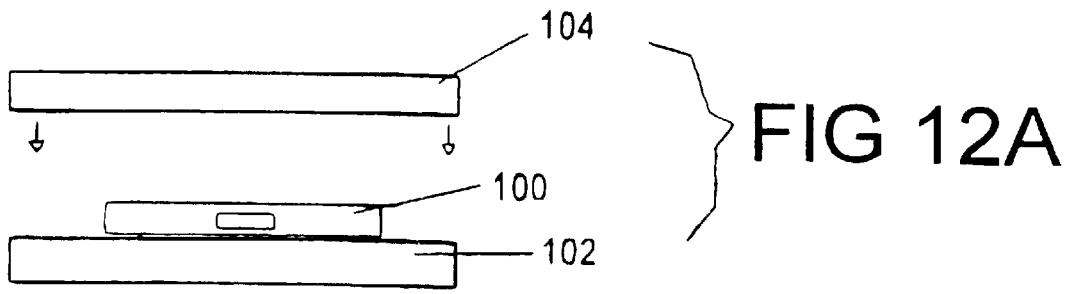
FIGS. 12A–C show the steps in forming a signaling or locating device using a magnetomechanical or magnetostrictive sensor element embedded in resin outer layers in which a gap or channel is formed between the sensor element and the resin layers by volumetric contraction of the resin as it solidifies.
Figure 12B:
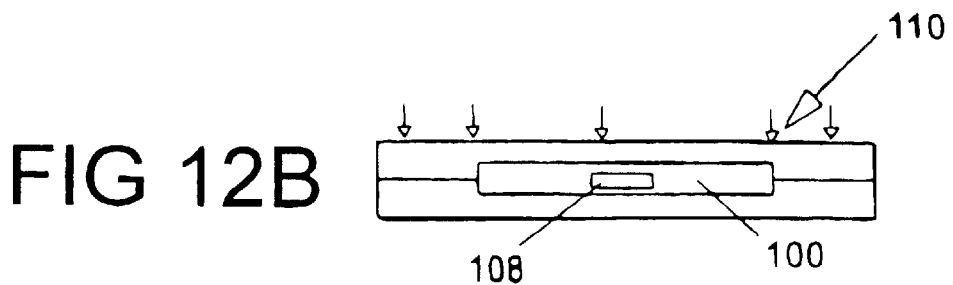
Figure 12C:
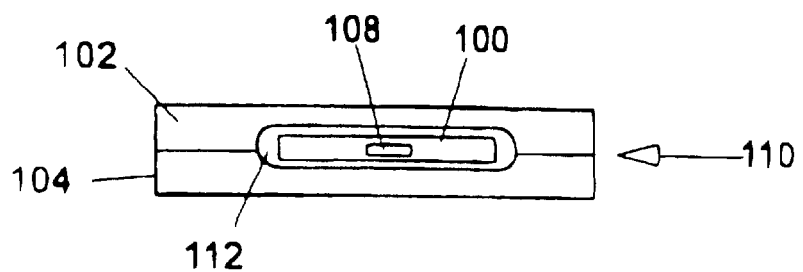

FIGS. 12A–C show the manner in which the marker element 100 can be embedded in methyl methacrylate, a material suitable for use in a denture without adversely affecting the mechanical vibration of the magnetomechanical target, especially a magnetic strip exhibiting vibrations due to the Barkhausen effiect. The first step in this example is to deposit a first layer 102 methyl methacrylate by mixing a liquid monomer with a polymer powder which are mixed in accordance conventional dental procedures. The layer can be deposited in a mold or on a surface or sheet having the same contour as the denture surface on which this signaling device or locator 110 is to be mounted. This layer is deposited in a concentration such that the methyl methacrylate has a soupy consistency. After the first layer of methyl methacrylate is deposited, the target 100 is positioned on the upper surface of this lower layer 102. The lower layer 102 extends beyond the marker 100 on all four lateral sides of the marker 100. The next step in this process is to deposit an upper layer 104 of methyl methacrylate on top of the marker 100. This upper layer 104 can be formed in the same manner as the lower layer 102 by mixing the liquid monomer with the liquid polymer. The upper layer 104 can be initially deposited on a second surface having a shape that will conform to the shape of the lower layer 102. The upper layer 104 is then positioned on top of the marker 110 and in contact with the lower layer 102. The upper layer 104 completely covers the upper surface of the marker 100 and extends beyond it on all sides. The upper layer 104 is also in contact with the lower layer 102 on all four sides so that the upper layer 104 can bond to the lower layer 102 on all four sides. The marker 100 will then be completely isolated, and will not come into contact with the oral cavity of the denture wearer when the locator element 110 is mounted on a denture.

The next step, illustrated in FIG. 12B is to apply pressure to the composite structure before the two layers 102 and 104 of methyl methacrylate polymerize to form a solid structure. Note that some of the methyl methacrylate material is permitted to laterally extrude as the composite structure is flattened and its thickness reduced. It has been demonstrated that a locator element or button 110 having a thickness of 1.30 mm (0.0510 inch) can be fabricated in this manner. The polymerization reaction between the liquid monomer and the power polymer, the constituents from which the methyl methacrylate structure is formed, will continue for both the upper layer 104 and the lower layer 102 until the composite structure solidifies.

Even though the fully polymerized methyl methacrylate in its solid form completely surrounds the magnetic marker, the magnetomechanical material 108 can still vibrate about its resonate frequency because a gap or channel 112 separating the magnetic material 108 from the solid layers 102 and 104 can be formed as illustrated in FIG. 12C. As the polymerization of the methyl methacrylate is completed and it solidifies, the methyl methacrylate will shrink due to the volumetric contraction which occurs during this reaction. The volume of solid polymer methacrylate material is less than the volume of the constituent liquid monomer and powder polymer that form this material. Thus the methyl methacrylate material will tend to shrink away from the embedded target 100 forming the gaps 112, because the methyl methacrylate will not adhere to the plastic material surrounding the magnetic material 108. The size of these gaps or channels 112 is not shown to scale in FIG. C, which is intended to be a schematic illustration only. The two layers 102 and 104 surrounding the strip 100 will not shrink away from each other or separate because they will form a bond as the material cures. In this manner, the strip 100 can be surrounded by a material that is suitable for use in a denture, but the vibration of the magnetomechanical material will not be adversely affected. This approach is believed to be of special importance with magnetic strips in which large mechanical stresses are induced in the magnetic material to enhance the detectable signal.

After the composite structure of the locator or signaling device 110 is formed in this manner, the outer resin layer can be trimmed to size. When installed in a denture, one exterior surface of the composite structure will be roughened and more liquid methyl methacrylate will be applied to bond the signaling device 110 to an exterior surface of the existing denture. Alternatively a roughened surface on a surface of one of the two layers can be formed by depositing the liquid and powder constituent materials on an external surface or in a mold having a roughened contour. Although the preferred embodiment depicted in this example is flat, it should be understood that the composite signaling device can be formed with a curvature that is suitable for securing the device 110 to the contour of a surface of the denture.

Figure 11:
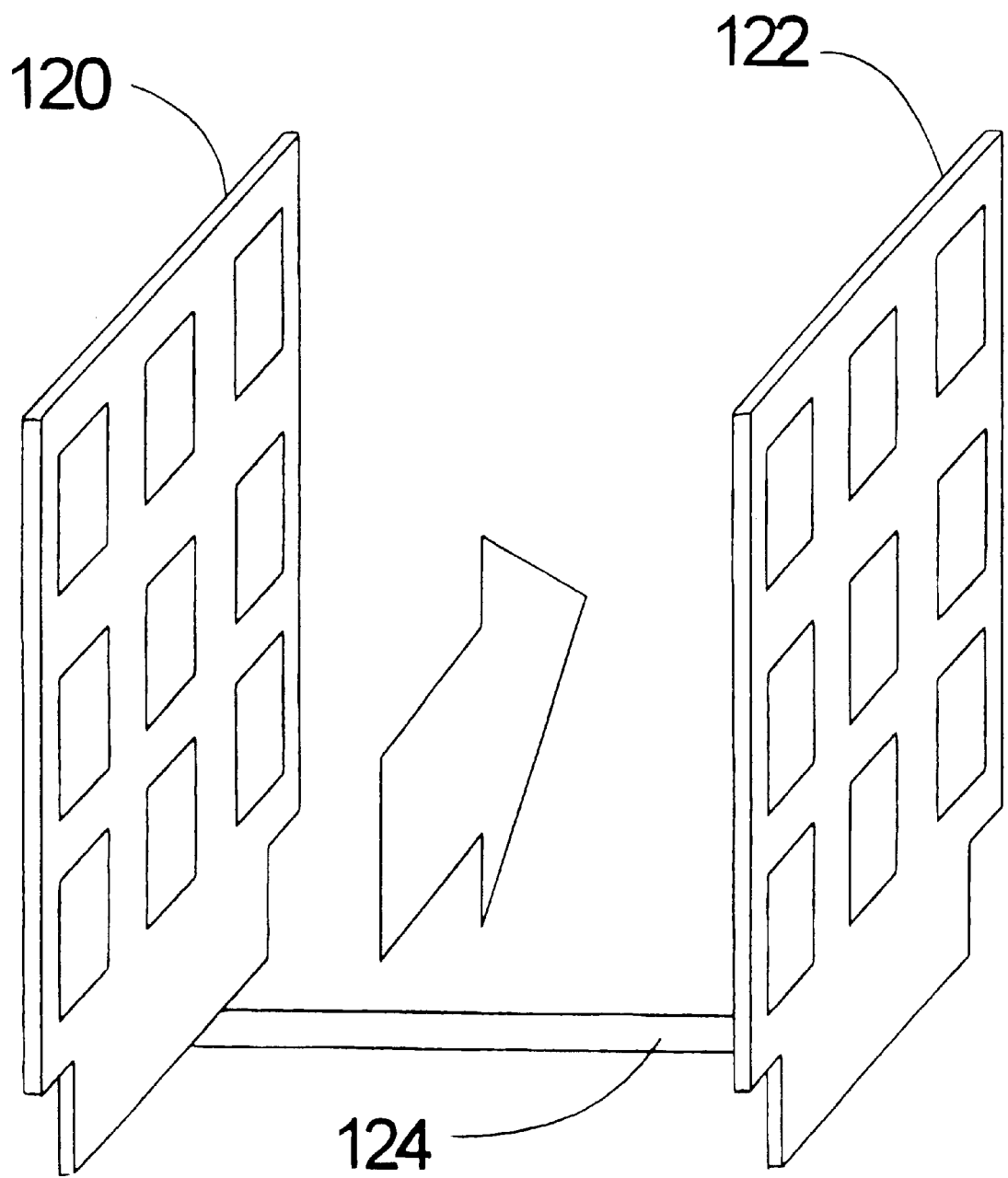
FIG. 11 is a view of two stationery transmitter-detector units that can be placed adjacent a trash or laundry facility or adjacent a door or entry into a trash or laundry area.

FIG. 11 shows stationery transmitter-detector units 120 and 122 that can be used to detect the strips 100 or 110. These stationery transmitter-detector units 120 and 122 are commercially available from Sentry Technology Corporation, and its subsidiary Knogo North America, Inc. and are referred to as Knoscape Micro Magnetic detection panels. Knoscape and Micro Magnetic are trademarks of Sentry Technology Corporation. Each of the transmitter-detector units 120 and 122 are both transmitters and detectors and can be positioned adjacent to a door or entry into a trash or laundry facility or area or any other area where dentures might be inadvertently lost. These transmitter-detector units can also be located adjacent to the trash receptacle or to the laundry apparatus. Two transmitter-detector units 120 and 122 of this type can be positioned at least three feet apart and they are joined by a low power cable 124. One of the units is attached to a standard electrical outlet, and an electronics box, not shown, containing suitable detection circuitry will be connected to the transmitter-detector units which serve as antennas. It has been found that denture units with targets 100 can be detected when large trash receptacles are rolled between transmitter-detector units 120, 122. Denture units with targets 100 attached can also be detected when a box containing the denture unit is thrown between the units 120, 122.

Figure 13:
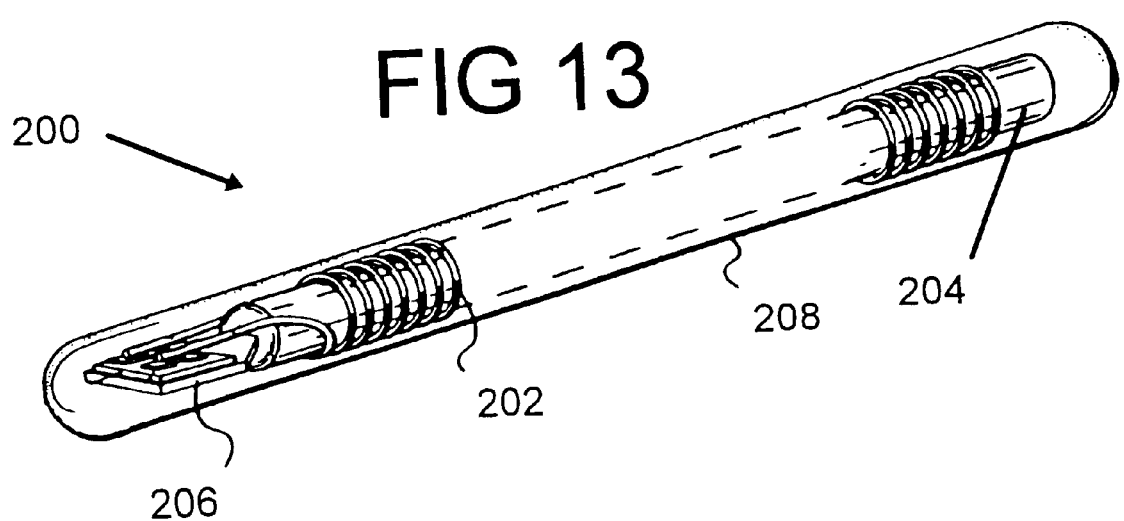
FIG. 13 is a view of an RFID tag that can be mounted in a denture.
Figure 14:
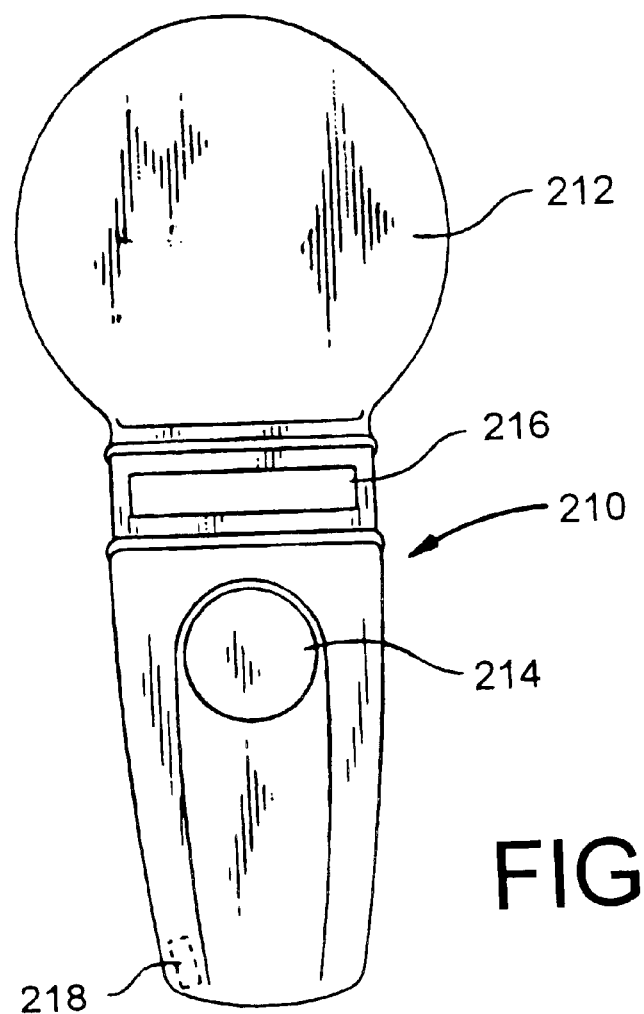
FIG. 14 is a view of a portable reader that can be used to locate an RFID tag, of the type shown in FIG. 13, embedded in a denture.
Figure 15A:
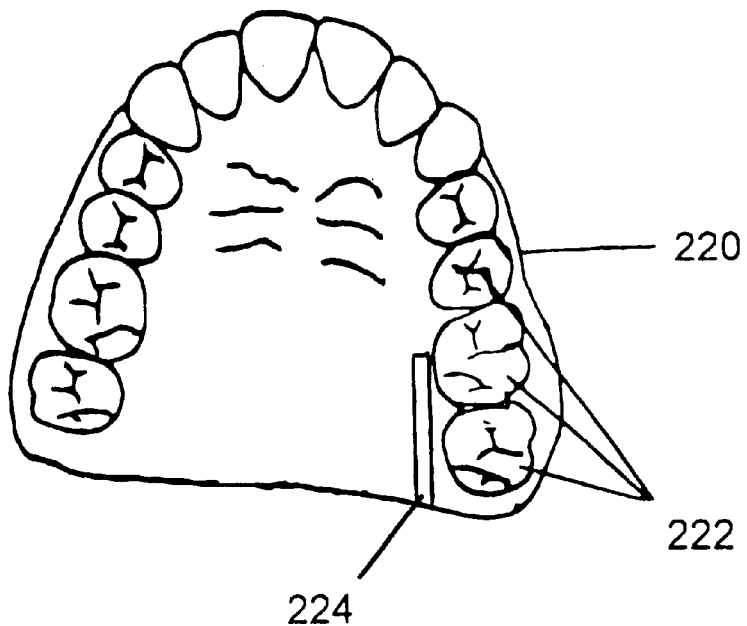
FIG. 15A is a view of an upper or maxillary denture in which a trough has been evacuated to receive an RFID, of the type shown in FIG. 13.
Figure 15B:
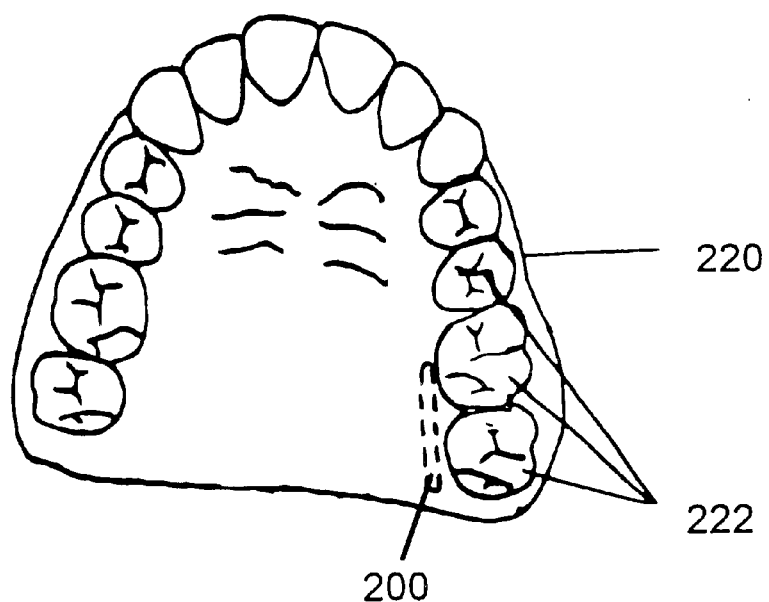
FIG. 15B shows the same maxillary denture after the RFID tag has been embedded in the denture by refilling the trench to form a smooth denture surface.
Figure 16A:
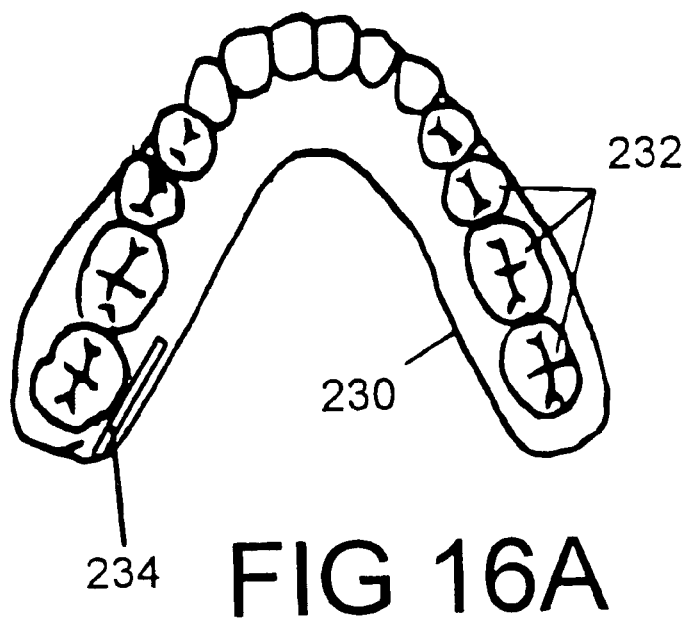
FIG. 16A is a view of a lower or mandibular denture in which a trough has been evacuated to receive an RFID tag, of the type shown in FIG. 13.
Figure 16B:
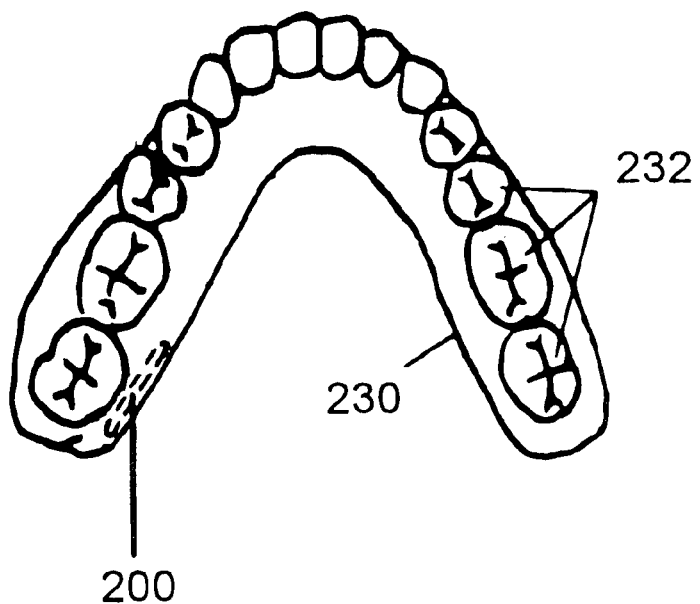
FIG. 16B is a view of the same mandibular denture after the RFID tag has been embedded in the denture by refilling the trench to form a smooth denture surface.
Figure 17:
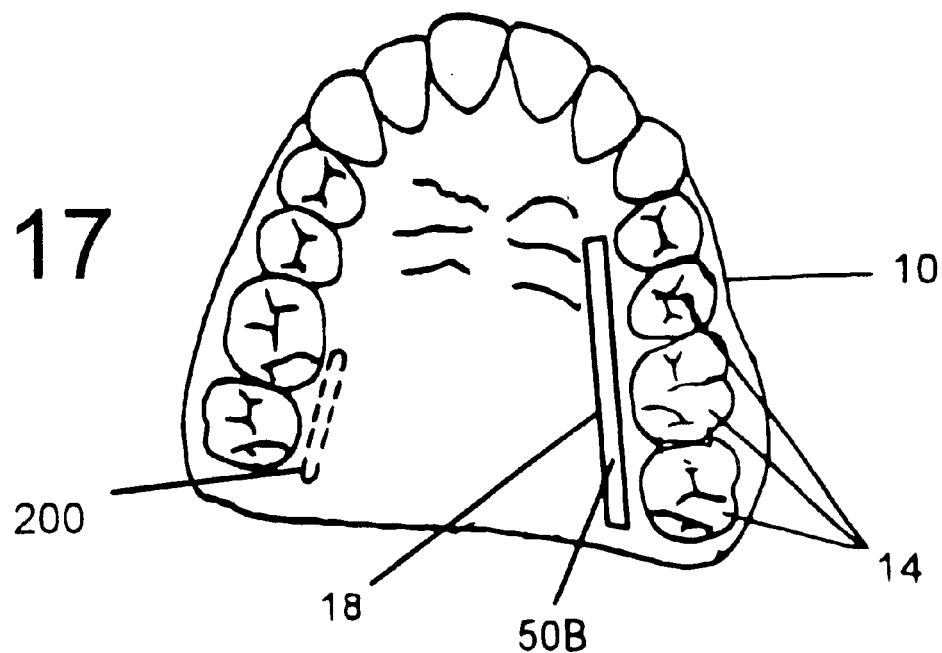
FIG. 17 is a view of a maxillary denture in which a magnetic conductive strip and an RFID tag have been embedded in different areas of the denture.
Figure 18:
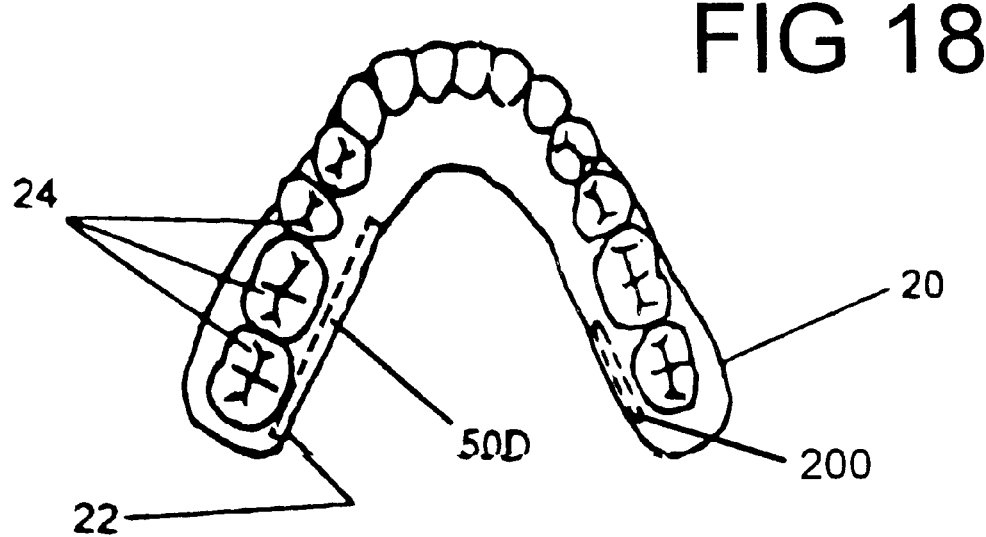
FIG. 18 is a view of a mandibular denture in which a magnetic conductive strip and an RFID tag have been embedded in different areas of the denture.

The magnetic locator strips shown in FIGS. 1–12 are not the only markers or tags that can be used to locate lost dentures. A radio frequency identification tag 200 is shown in FIG. 13. This tag 200 can be detected by a reader or detector 210 as shown in FIG. 14. FIGS. 15A and 15B show the manner in which one of these RFID tags 200 can be used with an upper or maxillary denture 220. FIGS. 16A and 16B show the manner in which the RFID tags 200 can be used in a lower or mandibular denture 230. The RFID tag 200 can also be used with a magnetic strip 50B in a maxillary denture as shown in FIG. 17 or with a magnetic strip 50D as shown in FIG. 18.

The radio frequency or RFID tag or passive transponder 200 shown in FIG. 13 includes an integrated circuit chip 206 that is connected to a coil or inductor 202, which surrounds a ferrite core 204. This subassembly is then encapsulated by a glass tube or envelope 208 which isolates the electronic subassembly from the surrounding environment, or conversely is suitable for protecting the vessel or the animate object with which the tag or transponder 200 is used. When the passive transponder 200 is placed in an electromagnetic excitation field generated by a reader or interrogator, such as portable reader 210, energy is inductively coupled through the coil 202 to power the integrated circuit component 206. The integrated circuit 206 comprises a logic component that when energized transmits a steam of pulses to the coil 202 which can in turn be detected by the reader 210. The pulses emitted by the logic component or integrated circuit chip 206 can either be in the form of a signal that is unique to each chip 306 or one that is more readily detectable by the reader 210. A unique ID number can be individually inscribed and programmed on the microchip 206 in the form of an alphanumeric identification code. Transponders of this type are manufactured by a number of different companies including Destron, Avid, Trovan, Nedap, Datamars, and Texas Instruments. These commercial transponders typically transmit an identification signal consisting of a string of ones and zeros in a number of different formats including FSK and PSK bit coding with Manchester and NRZ data encoding at bit rates ranging from 2500 BPS to approximately 8 K BPS. Transmit frequencies on the order of 125 kHz are common. The transmission of data between transponders 200 and readers 210 is described in more detail in U.S. Pat. No. 5,952,935, which is incorporated herein by reference. Transponders of this general type are also described in European Patent Specification 258 415.

The reader 210 used to locate the transponder 200 employs an antenna 212 and suitable transceiver electronics to both transmit an electromagnetic field at an appropriate excitation frequency and to detect the response from the transponder 200. The reader 210, shown in FIG. 14 is described in more detail in U.S. Pat. No. 5,952,935, which is again incorporated herein by reference. Battery powered reader or detector 210 also includes an on-off switch 214. When a response is received from the transponder 200, an ID number is displayed on an LCD 216. The reader also includes a data port 218 for transmitting data to other data processing equipment, such as a computer. Port 218 can be an RS 232 or EIA232 port.

Transponders 200 are available in different sizes. One commercially available transponder has a length of approximately 8–10 mm. Another transponder has dimensions of 18 mm by 3.5 mm. The smaller transponder can, at least in some circumstances, be detected at a range of up to 12 inches. The larger transponder can be detected, at a distance of 18–20 inches. These transponders or RFID tags conform to current ISO 11784 and ISO 11785 standards for B-Type devices. The transponders 200 can be detected by a representative transceiver or detector 210, shown herein as manufactured by Destron Fearing and referred to as the Pocket Reader EX® model. This particular version is not believed to be capable of detecting the transponder 200 at the maximum extent of these ranges. However, other hand held portable readers or scanners that are also available from Destron Fearing employ a larger antenna and is believed to have a greater range. An 18 mm by 3.5 mm microchip tag embedded in a denture has been detected at range of from 8–12 inches using a 2001F Portable Reader also manufactured by Destron Fearing. Stationary units are also available that have a greater range and it is believed that transponders of this type can be detected within a 24 inch by 24 inch area. Stationary units capable of maximum range are comparatively expensive and are therefore not believed suitable for use in locating lost dentures within a rest home, hospital or other medical or health care institution.

Transponders 200 can be embedded in existing maxillary and mandibular dentures. They can also be embedded in dentures during the original construction of the dentures. FIGS. 15A and 15B show one way in which a transponder 200 can be embedded in a maxillary or upper denture. The thickest portion of the base of a maxillary denture 220 is along the lingual surface on the interior of the molars 222. A trench 224, have a depth and length sufficient to accommodate a transponder 200 can be evacuated along this surface of the denture using conventional tools. The transponder 200 can then be positioned in this trench 224 and denture material such as methyl methacrylate. The filled area can then be smoothed to conform to the original contour of the lingual flange of the 220 denture with the transponder completely embedded in the denture 220. The methyl methacrylate used to fill in the trench 224 and to surround the transponder can be the same color as the rest of the denture so that the transponder will not be as visible as if a clear acrylic had been used, although the outline of the transponder can still be seen so that it can be located for scanning, and a person who finds the denture, when lost, can see that it bears an identifying transponder 200.

Although it is preferred that the transponder 200 be embedded on the interior or along the lingual flange of the maxillary denture, the transponder 200 can also be embedded along the exterior portion of the denture below the molars and adjacent the rear of the denture or adjacent the portion of the denture adjacent to the rear molars. It is possible to embed either the smaller 8–10 mm transponder or tag or the larger 18 mm by 3.5 mm transponder or tag in this area.

One technique for positioning the transponder 200 in the trench 224 is to use a syringe to place the transponder 200 in the trench 224. At least some commercially available transponders of this type are packaged in a syringe. Evacuating the trench 224 to the rear end of the maxillary denture 220 simplifies use of the syringe to place the transponder 200.

FIG. 16A shows the position of a trench 234 in a mandibular or lower denture 230. Here to the trench 234 is located on one lingual surface adjacent to molars 232. For mandibular dentures 230 this area is also the thickest part of the denture base. Trench 234 is also evacuated to a depth and length sufficient for placement of a transponder 200, and the trench extends to the rear edge of denture 230 to simplify placement of the transponder 200 using a syringe. FIG. 16B shows the same mandibular denture after the transponder 200 has been covered by dental acrylic.

The transponder 200 can be easily installed or embedded in a denture in not more than 15 minutes. This includes the step of evacuating the trench or channel followed by the steps of filling the trench or channel with dental acrylic or other suitable material and smoothing the dental acrylic to conform to the surrounding denture. This also includes the time for completion of the polymerization reaction so that the newly deposited material will have essentially the same characteristics as the original denture material. Of course this last step does not require involve a dentist or a dental technician, who is then free to attend to other matters.

The transponder 200 provides a simple method of identifying the specific denture when it is found. The unique code stored in the memory of the integrated circuit can be recorded or cross referenced on a database maintained either locally or on a network accessible database or through the Internet. The portable detector 210 can also be used as a locating device for a denture containing a transponder 200. Although the detectable range may differ, in some cases portable detectors of the general type represented by scanner 210 can be used to detect transponders at a range of 6–8 inches. Perhaps more common is a range of approximately 2 inches. Even this range can be sufficient to find a denture that may have been lost in bed linens, on table tops or under garments in a closet. A portable scanner 210 can also be used to further isolate and find a denture that has been located with a garbage container. In other words, areas where there is a high likelihood that a denture may have been lost can be scanned using the portable detector 210, even with limited range. Short range portable detectors of this type can be especially useful in rest homes or nursing homes, where the denture wearer would commonly not venture from a relatively limited area. The portable detector could still be used for other purposes, for example to locate lost orthodontic devices.

FIGS. 17 and 18 show that a transponder 200 can also be used in conjunction with a magnetic strip 50B in a maxillary denture 10 or with a mandibular denture 20 containing a magnetic strip 50D. In these views the transponder 200 is located on the opposite side of the denture base from the magnetic strips 50B and 50D. Alternatively, both locating tags could be located along the same side. Neither of the two locating tags cause interference that would prevent detection of either tag by the detectors or scanners use separately. This configuration would allow use of a magnetic strip detector that has more range than one of the portable detectors 210 to find lost dentures at a relatively long range. Thus a magnetic strip detector located near a garbage disposal area, or in a laundry or in a kitchen could be used to alert a worker that a denture containing a magnetic strip is present in a large bag or a collection of dirty dishes. A portable scanner or reader 210 could then be used to locate a transponder 200 at closer range, thus eliminating the need to conduct a hand search or all of the garbage or soiled material within a bundle. It is believed that the use of the two separate passive tags or locators is more cost effective. Although transponders 200 may be detectable at the same distance as magnetic strips, the cost of stationary scanners or detectors have the ability to locate transponders as they pass through a doorway may be prohibitive. It may also be necessary to drive scanners for transponders 200 at such an intensity that interference and other problems may be created. Other magnetic components, such as rare earth magnets, can also be detected in the presence of a varying electromagnetic fields, and such devices, which have been used in dentures for other purposes, can increase the detection range.

The magnetic strips and RF transponders depicted herein can also be used to locate other devices, such as eyeglasses and hearing aids, as part of a complimentary system suitable for use in medical and health care institutions.

I claim:

1. A system for locating a lost denture comprising an RF passive transponder containing an integrated circuit device connected to a coil and a portable reader having a transceiver for emitting an electromagnetic field to generate a voltage in the coil so that a code stored on the integrated circuit device is then transmitted through the coil to the transceiver for initially detecting the presence of a lost denture containing an RF passive transponder in a localized area larger than the area in which the code stored in the integrated circuit device can be read wherein the denture also includes a magnetic member embedded in the denture and a stationary transmitter-detector for detecting the presence of the magnetic member in the lost denture, the range at which the magnetic member can be detected being greater that the range at which the RF passive transponder can be detected.

2. The system of claim 1 wherein the transponder is encapsulated in glass and is embedded in a base section of the denture.

3. The system of claim 1 wherein the passive transponder includes a ferrite core around which the coil extends.

4. The system of claim 1 wherein the stationary transmitter-detector can detect the presence of the magnetic member in the presence of the RF passive transponder and the portable reader can detect the presence of the RF passive transponder in the presence of the magnetic member.

5. A denture that can be located and identified when lost, comprising:
- a radio frequency transponder embedded within the denture, the transponder emitting a coded radio frequency signal when activated by an external electromagnetic field, the coded radio frequency signal comprising means for identifying a specific denture; and
- an electromagnetically actuated device also embedded within the denture, the electromagnetically actuated device emitting an electromagnetic signal when activated by an external electromagnetic field, the electromagnetic signal emitted by the electromagnetically actuated device being stronger than the coded radio frequency signal emitted by the radio frequency transponder so that the presence of the denture can be detected at a greater distance than possible for identifying the coded radio frequency signal.

6. The denture of claim 5 wherein the radio frequency transponder is activated to emit the coded radio frequency signal by a first external electromagnetic field and the electromagnetically actuated device is activated to emit the electromagnetic signal by a second external electromagnetic field that differs from the first external electromagnetic field.

7. The denture of claim 6 wherein the electromagnetically actuated device comprises a magnetic device and the electromagnetic signal is emitted in response to changes in magnetic characteristics of the magnetic device when placed in the second external electromagnetic field.

8. An assembly for locating a lost denture comprising:
- at least one signaling device secured to the denture, the device emitting a signal when the denture is located within an external electromagnetic field;
- a portable transmitter-receiver emitting a first electromagnetic field that activates a signaling device to emit a signal detectable by the portable transmitter-receiver when a signaling device is within a first distance from the portable transmitter-receiver; and
- a stationary transmitter-receiver emitting a second electromagnetic field that activates a signaling device to emit a signal detectable by the stationary transmitter-receiver when a signaling device is within a second distance from the stationary transmitter-receiver, the second distance being greater than the first distance so that the portable transmitter-receiver comprises means for searching for a lost denture and the stationary transmitter-receiver comprises means for detecting the denture passing through a fixed location prior to realization that the denture has been lost or misplaced.

9. The assembly of claim 8 wherein the portable transmitter-receiver activates a first signaling device and the stationary transmitter-receiver activates a second signaling device.

10. A method of mounting a passive transponder in a denture comprising the steps of evacuating a trench in an area of a denture base adjacent molars on the denture, the trench extending to a rear edge of the denture base so that one end of the trench is open, followed by the steps of placing the transponder in the trench and then filling the trench to secure the transponder in the denture base, wherein a syringe is used to place the transponder in the trench.

11. The method of claim 10 wherein the trench is filled to a depth to cover the transponder.

12. The method of claim 11 wherein the area surrounding the trench is contoured to conform to an area of the denture base surrounding the trench and the embedded transponder.

* * * * *